United States Patent [19]

Brietzke et al.

[11] Patent Number: 5,522,982
[45] Date of Patent: Jun. 4, 1996

[54] PROCESS FOR PREPARING 4,4'-DIMETHYL-1,1'-BINAPHTHYL

[75] Inventors: Stephan Brietzke, Altendiez; Hans Millauer, Eschborn, both of Germany

[73] Assignee: Hoechst Aktiengesellschaft, Frankfurt am Main, Germany

[21] Appl. No.: 411,475

[22] Filed: Mar. 28, 1995

[30] Foreign Application Priority Data

Mar. 30, 1994 [DE] Germany ............... 44 110 24

[51] Int. Cl.⁶ ..................... C25B 3/02
[52] U.S. Cl. ............ 205/413; 205/419; 205/462; 205/463
[58] Field of Search ............ 204/59 R, 72, 204/78

[56] References Cited

U.S. PATENT DOCUMENTS

| | | | |
|---|---|---|---|
| 3,437,570 | 4/1969 | Wisdom | 204/59 R |
| 4,101,392 | 7/1978 | Hallcher et al. | 204/72 |

OTHER PUBLICATIONS

Euroepan Search Report No. 95103744.9, dated Aug. 11, 1995.

Memoirs of the Niihama College of Technology Science & Engineering, Bd. 25, 1989, "Electrooxidation of 2–Methyl-naphthalene in Aqueous" no month.

Helv. Chim. ACTA, Bd. 11, 1928, Electrochemische Oxidation des alpha–Methyl–naphthalins.

Fichter et al, *Helvetica Chimica Acta, vol. 11, Basel at Geneva, Aedibus George & Co., pp.1265–1267 (1928) no month*.

Kumada, M., et al, "Cross–Coupling of Grignard Reagents" in vol. 28, *Organic Syntheses*, N. Y. John Wiley and Sons, 1978, pp. 127–133 no month.

McKillop, A., et al, *J. Am. Chem. Soc.* 102:6504–6512 (1980) no month.

*Primary Examiner*—John Niebling
*Assistant Examiner*—Edna Wang
*Attorney, Agent, or Firm*—Connolly and Hutz

[57] ABSTRACT

The invention relates to a process for preparing 4,4'-dimethyl-1,1'-binaphthyl, by electrochemically oxidatively dimerizing 1-methylnaphthalene in the presence of acetonitrile/water/conducting salt mixtures which additionally contain at least one further component which is immiscible or only partially miscible with water.

32 Claims, No Drawings

PROCESS FOR PREPARING 4,4'-DIMETHYL-1,1'-BINAPHTHYL

The present invention relates to a process for preparing 4,4'-dimethyl-1,1'-binaphthyl by electrolytic dimerization of 1-methylnaphthalene.

4,4'-dimethyl-1,1'-binaphthyl is an intermediate for polyamides, polyesters, optical brighteners and dyes.

The preparation of 4,4'-dimethyl-1,1'-binaphthyl by a chemical route can be carried out in principle by reductive coupling of 1-bromo-4-methylnaphthalene by the method of Kumada-Tamao (Org. Synth., Vol. 58, 127 (1978)). For this purpose, 1-bromo-4-methylnaphthalene is converted into the corresponding Grignard compound and subsequently coupled with 1-bromo-4-methylnaphthalene using a nickel-containing catalyst, for example $Ni(PPh_3)_2Cl_2$. The process gives as production waste a mixture of magnesium bromide and nickel salts which have to be separated and worked up.

An oxidative dehydrodimerization by a chemical route is described by McKillop et al. [J. Am. Chem. Soc. 102 (21) 6504-12].

Although the reaction proceeds very selectively, it has the disadvantage of the use of $Tl(COOCF_3)_3$ as reactant in equimolar (based on product) amount. Likewise disadvantageous is the use of trifluoroacetic acid (yield 85%) as solvent or tetrachloromethane (3 l/mol) boron trifluoride etherate (1 l/mol) (yield 93%).

A further oxidative dimerization process is carried out using oxygen over platinum/carbon or palladium/carbon in trifluoroacetic acid.

An electrochemical method is described by Fichter and Herszbein. (Helvetica Chimica Acta 11, 1265.)

The electrolyte used in this publication is a mixture of acetone and sulfuric acid, the anode is the reaction vessel made of preoxidized lead, the cathode is a tin stirrer. The electrolysis solution contains about 10% by weight of 1-methylnaphthalene, with a yield of 10.5% by weight of 4,4'-dimethyl-1,1'-binaphthyl being achieved. Owing to the apparatus required and its unsatisfactory efficiency, this method is not suitable for industrial applications.

There was therefore a great need for a process which, starting out from readily available starting materials, makes 4,4'-dimethyl-1,1'-binaphthyl available in high yield and purity.

This object is achieved by a process for preparing 4,4'-dimethyl-1,1'-binaphthyl, which comprises electrochemically oxidatively dimerizing 1-methylnaphthalene in the presence of acetonitrile/water/conducting salt mixtures which additionally contain at least one further component which is immiscible or only partially miscible with water.

The electrochemical process proceeds according to the following reaction equation:

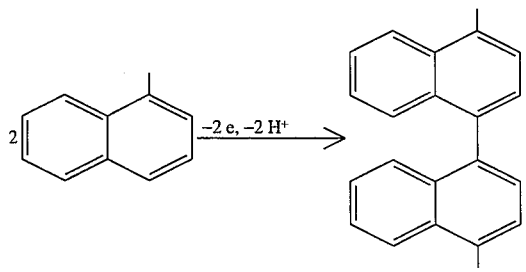

The reaction proceeds highly selectively when carried out according to the invention, the yield is about 50% of theory.

The electrolyte systems used for the process of the invention can be formed in various ways. Fundamentally, however, acetonitrile, water, a conducting salt and at least one further component which is immiscible or only partially miscible with water always participate in the makeup of such electrolyte systems.

The water-immiscible component can be (a) an aliphatic or cycloaliphatic hydrocarbon such as, for example, pentane, hexane, cyclohexane, methylcyclohexane, heptane, octane, isooctane, decane, dodecane or decalin or mixtures (distillation fractions) of such compounds, or (b) an aromatic hydrocarbon such as, for example, benzene, toluene, o-, m- or p-xylene, mesitylene, naphthalene or tetralin, or (c) a halogenated hydrocarbon such as, for example, methylene chloride or chlorobenzene, or (d) a ketone having from about 5 to 10 carbon atoms such as, for example, diethyl ketone, methyl t-butyl ketone or acetophenone.

This component should have a boiling point above the respective reaction temperature.

Use is preferably made of aliphatic, cycloaliphatic or aromatic hydrocarbons having from 6 to 10 carbon atoms; particular preference is given to heptane and toluene. The water-immiscible component of the electrolyte system can also be a mixture of two or more of the above-mentioned compounds.

Suitable conducting salts for the process of the invention are the alkali metal, alkaline earth metal, ammonium, monoalkylammonium, dialkylammonium, trialkylammonium or tetraalkylammonium salts of acids whose complex anions are derived from hexavalent sulfur, from pentavalent phosphorus or from trivalent boron. Mixtures of a plurality of the specified conducting salts can likewise be used.

Use can be made, for example, of the salts of the following anions: hydrogensulfate, methylsulfate, ethylsulfate, methanesulfonate, ethanesulfonate, propanesulfohate, butanesulfonate, octanesulfonate, benzenesulfonate, toluenesulfonate, 2-chlorobenzenesulfonate, p-chlorobenzenesulfonate, 2,4-dichlorobenzenesulfonate, naphthalene-1-sulfonate, naphthalene-2-sulfonate; methanephosphonate, ethanephosphonate, propanephosphonate, butanephosphonate, hexafluorophosphate; tetrafluoroborate; further suitable salts are those of alkanesulfonic acids or alkanephosphonic acids whose alkyl radical is polyfluorinated or perfluorinated, such as, for example, trifluoromethanesulfonate, 1,1,2,3,3,3-hexafluoropropanesulfonate, nonafluorobutanesulfonate, heptadecafluorooctanesulfonate, trifluoromethanephosphonate, nonafluorobutanephosphonate.

It has been found to be useful in many cases to use sodium or tetraalkylammonium salts (containing alkyl radicals having from 1 to 4 carbon atoms) of alkanesulfonic acids (containing alkyl radicals having from 1 to 8 carbon atoms or containing polyfluorinated or perfluorinated alkyl radicals having from 1 to 4 carbon atoms), of arylsulfonic acids (with aryl=phenyl, naphthyl; alkyl-substituted or chloro-substituted phenyl), of tetrafluoroboric acid and hexafluorophosphoric acid, as conducting salts.

Preferred conducting salts are sodium or tetraalkylammonium tetrafluoroborate.

The mixing ratio of acetonitrile to water in the electrolytes used is in the range from 100:1 to 1:1; it has been found to be favorable to work in the range from 20:1 to 2:1. The amount of the component which is immiscible or only partially miscible with water is, based on the total weight of the electrolyte, in the range from 10 to 90%; preference is given to the range from 30 to 80%.

The amount of the conducting salt is, based on the total weight of the electrolyte, in the range from 0.5 to 15%; preference is given to the range from 1 to 7%.

The mixing ratios of the components of the electrolyte are preferably set in such a way that there is formed a two-phase system in which water and conducting salt are either present in the acetonitrile phase or exist largely separated from the organic phase as independent phase, with different proportions of the conducting salt being in principle to be found in the two phases. However, a single-phase reaction procedure is also possible.

The process is carried out in an undivided electrolysis cell. For relatively large electrolyses, preference is given to using flow-through cells having a stack of electrodes arranged in a bipolar manner. Suitable anode materials are graphite, vitreous carbon, platinum or stainless steel; stainless steel anodes are preferred. The cathode material is not critical. All customary metals such as, for example, steel, stainless steel, nickel, titanium, copper, platinum and also graphite or vitreous carbon can be used; stainless steel is preferred.

The process of the invention is carried out at current densities in the range from 10 to 250 mA/cm$^2$, preferably in the range from 25 to 150 mA/cm$^2$ and particularly preferably in the range from 40 to 100 mA/cm$^2$.

The electrolysis is generally carried out at temperatures between 0° and 80° C.; a preferred temperature range is between 50° and 65° C.

The target compound is only sparingly soluble in most electrolyte systems at room temperature and, after the reaction is complete, can be obtained in coarse crystalline form by cooling the reaction mixture and can subsequently be isolated by filtration.

Particular advantages of the process of the invention are that expensive intermediates such as 1-bromo-4-methylnaphthalene and problematical wastes containing heavy metals are avoided and the isolation of the product and also the recycling of unreacted raw material, solvents and conducting salts are possible by simple means.

The process gives the product in improved current and material yields and achieves industrially utilizable conversions.

The process can also be carried out in a flow-through cell.

The following examples illustrate the invention without limiting it thereto.

EXAMPLE

1.
   Starting material: 170 g of 1-methylnaphthalene (1.2 mol)
   Electrolyte: 1500 ml of acetonitrile/1500 ml of n-heptane
   Additives: 75 ml of methanol/75 ml of water
   Conducting salt: 15 g of NaBF$_4$
   Reaction Temperature: 50° C.
   Cell: Undivided laboratory flow-through cell U7
   Anode: Graphite
   Cathode: Stainless steel
   Electrode area: 200 cm$^2$
   Current density: 50 mA/cm$^2$
   Transmitted charge: 64 Ah (200% of theory)
   Conversion: 59%
   Yield: 40%

2.
   Starting material: 200 g of 1-methylnaphthalene (1.4 mol)
   Electrolyte: 1500 ml of acetonitrile/1500 ml of n-heptane
   Additives: 100 ml of water
   Conducting salt: 30 g of NaBF$_4$
   Reaction Temperature: 55° C.
   Cell: Undivided laboratory flow-through cell U7
   Anode: Stainless steel
   Cathode: Stainless steel
   Electrode area: 200 cm$^2$
   Current density: 50 mA/cm$^2$
   Transmitted charge: 63 Ah (166% of theory)
   Conversion: 75%
   Yield: 51%

3.
   Starting material: 300 g of 1-methylnaphthalene (2.11 mol)
   Electrolyte: 2000 ml of acetonitrile/500 ml of toluene (single-phase)
   Additives: 200 ml of water
   Conducting salt: 25 g of NaBF$_4$
   Reaction Temperature: 60° C.
   Cell: Undivided laboratory flow-through cell U7
   Anode: Graphite
   Cathode: Stainless steel
   Electrode area: 200 cm$^2$
   Current density: 50 mA/cm$^2$
   Transmitted charge: 56.5 Ah (100% of theory)
   Conversion: 34%
   Yield: 21%

4.
   Starting material: 56.8 g of 1-methylnaphthalene (0.4 mol)
   Electrolyte: 250 ml of acetonitrile/250 ml of heptane
   Additives: 12 ml of water/12 ml of methanol
   Conducting salt: 5 g of NaBF$_4$
   Reaction Temperature: 20° C.
   Cell: Pot cell, 500 ml, undivided
   Anode: Graphite EH
   Cathode: Stainless steel mesh
   Electrode area: 50 cm$^2$
   Current density: 50 mA/cm$^2$
   Transmitted charge: 10.7 Ah (100% of theory)
   Conversion: 32%

5.
   Starting material: 28.6 g of 1-methylnaphthalene (0.2 mol)
   Electrolyte: 250 ml of acetonitrile/250 ml of heptane
   Additives: 12 ml of water
   Conducting salt: 5 g of NaBF$_4$
   Reaction Temperature: 52° C.
   Cell: Pot cell, 500 ml, undivided
   Anode: Stainless steel mesh
   Cathode: Stainless steel mesh
   Electrode area: 50 cm$^2$
   Current density: 50 mA/cm$^2$
   Transmitted charge: 10.7 Ah (200% of theory)
   Conversion: 83%
   Workup:
   After cooling, the crystalline solid is filtered off from the reaction mixture and recrystallized from acetone.
   Melting point: 148° C. (uncorrected)

We claim:

1. A process for preparing 4,4'-dimethyl-1, 1'-binaphthyl, which comprises electrochemically oxidatively dimerizing 1-methylnaphthalene in the presence of a mixture of acetonitrile, water, conducting salt, and at least one additional component which is immiscible or only partly miscible with water in an amount of at least 10% by weight.

2. The process as claimed in claim 1, wherein the water-immiscible component is an aliphatic or cycloaliphatic hydrocarbon; an aromatic hydrocarbon; a halogenated hydrocarbon; a ketone or a mixture of the above mentioned compounds.

3. The process as claimed in claim 2, wherein the aliphatic or cycloaliphatic hydrocarbon is pentane, hexane, cyclohexane, methylcyclohexane, heptane, octane, isooctane, decane, dodecane, or decalin.

4. The process as claimed in claim 2, wherein the aromatic hydrocarbon is benzene, toluene, o-, m-, p-xylene, mesitylene, naphthalene or tetralin.

5. The process as claimed in claim 2, wherein the halogenated hydrocarbon is methylene chloride or chlorobenzene.

6. The process as claimed in claim 2, wherein the ketone contains from 5 to 10 carbon atoms.

7. The process as claimed in claim 1, wherein the water-immiscible component has a boiling point above the respective reaction temperature.

8. The process as claimed in claim 1, wherein the conducting salt is an alkali metal, alkaline earth metal, ammonium, monoalkylammonium, dialkylammonium, trialkylammonium or tetraalkylammonium salts of acids whose anions are derived from hexavalent sulfur, pentavalent phosphorous, or trivalent boron, or mixtures thereof.

9. The process as claimed in claim 8, wherein the anions are selected from the group consisting of hydrogensulfate, methylsulfate, ethylsulfate, methanesulfate, ethanesulfonate, propanesulfonate, butanesulfonate, octanesulfonate, benzenesulfonate, toluenesulfonate, 2-chlorobenzenesulfonate, p-chlorobenzenesulfonate, 2,4-dichlorobenzenesulfonate, naphthalene-1-sulfonate, naphthalene-2-sulfonate, methanephosphonate, ethanephosphonate, propanephosphonate, butanephosphonate, hexafluorophosphate, and tetrafluoroborate.

10. The process as claimed in claim 1, wherein the conducting salt is selected from the group consisting of a salt of an alkanesulfonic acid whose alkyl radical is polyfluorinated or perfluorinated and a salt of an alkanephosphonic acid whose alkyl radical polyfluorinated or perfluorinated.

11. The process as claimed in claim 1, wherein the conducting salt is a sodium or tetraalkylammonium salt containing alkyl radicals having from 1 to 4 carbon atoms, a salt of alkanesulfonic acids containing alkyl radicals having from 1 to 8 carbon atoms or containing polyfluorinated or perfluorinated alkyl radicals having from 1 to 4 carbon atoms, a salt of arylsulfonic acids with aryl=phenyl, naphthyl, alkyl-substituted or chloro-substituted phenyl, or a salt of tetrafluoroboric acid and a salt of hexafluorophosphoric acid.

12. The process as claimed in claim 1, wherein the conducting salt used is sodium or tetraalkylammonium tetrafluoroborate.

13. The process as claimed in claim 1, wherein acetonitrile and water are present in a ratio of from 100:1 to 1:1.

14. The process as claimed in claim 1, wherein the component which is immiscible or only partly miscible with water is present in an amount of from 10 to 90% by weight, based on the total amount of the acetonitrile, water, conducting salt, and component which is immiscible or only partly miscible with water.

15. The process as claimed in claim 1, wherein the conducting salt is present in an amount of from 0.5 to 15% by weight, based on the total weight of the acetonitrile, water, conducting salt, and component which is immiscible or only partly miscible with water.

16. The process as claimed in claim 1, wherein the dimerizing is carried out by electrolysis at current densities of from 10 to 250 mA/cm$_2$.

17. The process as claimed in claim 1, wherein the dimerizing is carried out by electrolysis at temperatures of from 0° to 80° C.

18. The process as claimed in claim 1, wherein the dimerizing is conducted by electrolysis with an anode, and the anode comprises graphite, vitreous carbon, platinum, or stainless steel.

19. The process as claimed in claim 1, wherein the dimerizing is conducted by electrolysis with a cathode, and the cathode comprises graphite, vitreous carbon, platinum, or stainless steel.

20. The process as claimed in claim 3, wherein the aliphatic or cycloaliphatic hydrocarbon has from 6 to 10 carbon atoms.

21. The process as claimed in claim 3, wherein the aliphatic or cycloaliphatic hydrocarbon is heptane or octane.

22. The process as claimed in claim 4, wherein the aromatic hydrocarbon has from 6 to 10 carbon atoms.

23. The process as claimed in claim 4, wherein the aromatic hydrocarbon is toluene or xylene.

24. The process as claimed in claim 6, wherein the ketone is diethyl ketone, methyl tert-butyl ketone, or acetophenone.

25. The process as claimed in claim 10, wherein the conducting salt is selected from the group consisting of trifluoromethanesulfonate, 1,1,2,3,3,3-hexafluoropropanesulfonate, nonafluorobutanesulfonate, heptadecafluorooctanesulfonate, trifluoromethanephosphonate, and nonafluorobutanephosphonate.

26. The process as claimed in claim 1, wherein the acetonitrile and water are present in a ratio of from 20:1 to 2:1.

27. The process as claimed in claim 1, wherein the component which is immiscible or only partly miscible with water is present in an amount of from 30 to 80% by weight, based on the total weight of the acetonitrile, water, conducting salt, and component which is immiscible or only partly miscible with water.

28. The process as claimed in claim 1, wherein the conducting salt is present in an amount of from 1 to 7% by weight, based on the total weight of the acetonitrile, water, conducting salt, and component which is immiscible or only partly miscible with water.

29. The process as claimed in claim 1, wherein the dimerizing is carried out by electrolysis at current densities of from 25 to 150 mA/cm$^2$.

30. The process as claimed in claim 1, wherein the dimerizing is carried out by electrolysis at current densities of from 40 to 100 mA/cm$^2$.

31. The process as claimed in claim 1, wherein the dimerizing is carried out by electrolysis at temperatures of from 50° to 65° C.

32. The process as claimed in claim 1, wherein the dimerizing is carried out by electrolysis using a cathode and anode, and the cathode or anode is stainless steel.

* * * * *